US010821432B2

(12) United States Patent
Park et al.

(10) Patent No.: US 10,821,432 B2
(45) Date of Patent: Nov. 3, 2020

(54) OLEFIN PRODUCTION METHOD COMPRISING REDUCTION PRETREATMENT

(71) Applicants: SK GAS CO., LTD., Seongnam-si, Gyeonggi-do (KR); KOREA RESEARCH INSTITUTE OF CHEMICAL TECHNOLOGY, Daejeon (KR)

(72) Inventors: Deuk Soo Park, Goyang-si (KR); Ung Gi Hong, Seongnam-si (KR); Hyeongchan Ahn, Seoul (KR); Won Choon Choi, Daejeon (KR); Yong Ki Park, Seoul (KR)

(73) Assignees: SK GAS CO., LTD., Seongnam-si (KR); KOREA RESEARCH INSTITUTE OF CHEMICAL TECHNOLOGY, Daejeon (KR)

( * ) Notice: Subject to any disclaimer, the term of this patent is extended or adjusted under 35 U.S.C. 154(b) by 0 days.

(21) Appl. No.: 16/468,204

(22) PCT Filed: May 1, 2018

(86) PCT No.: PCT/KR2018/005046
§ 371 (c)(1),
(2) Date: Jun. 10, 2019

(87) PCT Pub. No.: WO2018/225951
PCT Pub. Date: Dec. 13, 2018

(65) Prior Publication Data
US 2019/0388884 A1    Dec. 26, 2019

(30) Foreign Application Priority Data
Jun. 7, 2017 (KR) .................. 10-2017-0070868

(51) Int. Cl.
*B01J 37/16* (2006.01)
*C07C 5/32* (2006.01)
(Continued)

(52) U.S. Cl.
CPC ............. *B01J 37/16* (2013.01); *B01J 35/026* (2013.01); *C07C 5/32* (2013.01); *C07C 11/06* (2013.01)

(58) Field of Classification Search
CPC .......... B01J 37/16; B01J 35/026; C07C 5/32; C07C 5/324; C07C 11/06; C07C 2521/04; C07C 2521/06; C07C 2523/26; C07C 9/08
See application file for complete search history.

(56) References Cited

U.S. PATENT DOCUMENTS

| | | | |
|---|---|---|---|
| 2008/0194891 A1* | 8/2008 | Pretz ..................... | C07C 5/3332 585/252 |
| 2011/0230698 A1* | 9/2011 | Towler .................. | C07C 5/3332 585/661 |
| 2017/0313636 A1* | 11/2017 | Wang .................... | C07C 5/3335 |

FOREIGN PATENT DOCUMENTS

| KR | 10-1988-0000362 A | 3/1988 |
|---|---|---|
| KR | 10-0651418 B1 | 11/2006 |

(Continued)

OTHER PUBLICATIONS

International Search Report for PCT/KR2018/005046 dated Sep. 5, 2018 from Korean Intellectual Property Office.

*Primary Examiner* — Youngsul Jeong
*Assistant Examiner* — Jason Y Chong
(74) *Attorney, Agent, or Firm* — Paratus Law Group, PLLC

(57) ABSTRACT

Disclosed is an olefin production method including: pretreating a catalyst by providing reduction gas to an alumina type catalyst to produce olefin from the hydrocarbon including not less than 90 wt % of LPG (Stage 1); producing the (Continued)

olefin by providing the catalyst pretreated at Stage 1 into Riser of Fast Fluidization Regime to dehydrogenate the hydrocarbon (Stage 2); separating the mixture of the produced propylene and the catalyst used at Stage 2, and regenerating the separated catalyst (Stage 3); and recycling the catalyst regenerated at Stage 3 to the process of Stage 1 (Stage 4).

15 Claims, 5 Drawing Sheets

(51) Int. Cl.
*B01J 35/02* (2006.01)
*C07C 11/06* (2006.01)

(56) References Cited

FOREIGN PATENT DOCUMENTS

| KR | 10-2016-0071114 A | 6/2016 |
| KR | 10-2017-0003371 A | 1/2017 |
| KR | 10-2017-0007636 A | 1/2017 |

* cited by examiner

OLEFIN PRODUCTION METHOD COMPRISING REDUCTION PRETREATMENT

CROSS REFERENCE TO PRIOR APPLICATIONS

This application is a National Stage Patent Application of PCT International Patent Application No. PCT/KR2018/005046 (filed on May 1, 2018) under 35 U.S.C. § 371, which claims priority to Korean Patent Application No. 10-2017-0070868 (filed on Jun. 7, 2017), which are all hereby incorporated by reference in their entirety.

BACKGROUND

The present invention relates to an olefin production method comprising a circulating fluidized bed process comprising reduction pretreatment.

The olefin like ethylene and propylene is widely used in the petrochemical industry. The olefin can be generally produced from naphtha thermal cracking process. However, because the competitiveness of the process using low-grade hydrocarbon as a raw material becomes higher according to shale gas revolution, on-purpose olefin production method using the catalytic dehydrogenation process is needed.

The catalytic dehydrogenation process for producing the olefin utilizes various low-grade hydrocarbon compound as a raw material, and the olefin yield is very good. However, although a commercial fixed bed dehydrogenation process has the high olefin yield at an initial stage of the reaction of the hydrocarbon contacting with the catalyst, the hydrocarbon conversion rate and the olefin yield decreases and the energy consumption for the regeneration process is increased because of the catalyst deactivation and the excessive coke generation as time goes. In order to solve the problem, the circulating fluidized bed process to have a short contact time of the hydrocarbon and the catalyst is suggested.

However, at an initial stage of the circulating fluidized bed process to have a short contact time of the hydrocarbon and the catalyst, the hydrocarbon reacts with the catalyst to generate the byproduct rapidly other than the olefin. Therefore, there is a demerit that the conversion rate of the hydrocarbon is high but the selectivity of the olefin is very low.

At the circulating fluidized bed process to produce the olefin from the hydrocarbon feedstock, in order to selectively produce the olefin such as ethylene and propylene with high conversion rate and high selectivity, setting the operation condition of Riser mainly conducting the dehydrogenation reaction can be considered as an important factor. Especially, the fluid flow phenomena and the reaction phenomena in Riser can be easily understood by the following theoretical study, which is explained hereinafter in detail.

As shown in FIG. 1, when the gas is provided from the bottom to the reactor charged with the solid catalyst, if particles are fluidized and go over Minimum Fluidization Velocity, the flow regime would be classified into five (5) regimes.

Specifically, the regimes are named as Minimum Fluidization Regime, Bubbling Fluidization Regime, Slugging Fluidization Regime, Turbulent Fluidization Regime and Lean phase Fluidization with Pneumatic Conveying Regime, and the particle motion property in each regime is different from each other.

Therefore, in case of the process using the fluidized bed reactor, the suitable fluidized flow regime for each process property is formed and operated.

FIG. 2 shows that the change of the catalyst volume fraction is described according to the height of Riser, that is, the change of the flow regime. It is verified that the catalyst volume fraction in the reactor is changed according to the change of the fluidized flow regime. By the way, because the catalyst volume fraction importantly affects the process performance at the catalytic reaction such as the fluidized contact dehydrogenation reaction, consequently, the process operation condition to determine the fluidized flow regime dominating the catalyst volume fraction in the reactor influences very importantly on the reaction result.

In order to determine the fluidized flow regime in Riser of the circulating fluidized bed process, the following factors must be considered. These factors are, for example, catalyst size, catalyst circulating rate, ratio of feed and catalyst, catalyst strength, etc.

In addition, the following factors directly affecting the dehydrogenation reaction must be considered. These factors are, for example, reaction temperature, the amount of absorption heat of the reaction, reaction time, ratio of feed and catalyst, catalyst deactivation caused by the coke generation, etc.

However, despite the process to limit the contact time of the hydrocarbon and the catalyst, at an early stage of the reaction, the hydrocarbon reacts with the catalyst to rapidly generate the byproduct such as carbon dioxide, carbon monoxide, etc., other than olefin. Therefore, while the conversion rate of feed is high, the selectivity is very low. Also, because the process stability to directly affect the catalyst life span is low, there still remains the problem that total process performance is disadvantageously influenced.

At this, during studying the olefin production method using the circulating fluidized bed process with the higher economic efficiency and the productivity than the traditional production process, by applying newly developed catalyst and introducing the catalyst reduction process to provide the reduction gas such as hydrocarbon to the part from Catalyst Regenerator to the bottom of Riser, more efficient olefin production method is developed and the present invention is completed. The present invention has the higher olefin selectivity, decreases the byproduct generation, saves the energy cost to increase the catalyst reaction temperature, and decreases the equipment investment cost.

SUMMARY

The present invention provides a circulating fluidized bed olefin production method with the higher economic efficiency and the productivity than the traditional process.

The olefin production method of the present invention using a circulating fluidized bed process and comprising a reduction pretreatment comprises: (Stage 1) pretreating a catalyst by providing reduction gas to an alumina type catalyst to produce the olefin from the hydrocarbon including not less than 90 wt % of LPG; (Stage 2) producing the olefin by providing the catalyst pretreated at Stage 1 into Riser of Fast Fluidization Regime to dehydrogenate the hydrocarbon; (Stage 3) separating the mixture of produced propylene and the catalyst used at Stage 2, and regenerating the catalyst; and (Stage 4) recycling the catalyst regenerated at Stage 3 to the process of Stage 1.

The pretreatment of Stage 1 can comprise at least one of i) reduction treatment from the end of Regenerator to Catalyst Provider, and ii) reduction treatment from Catalyst Provider to the bottom of Riser.

The pretreatment of Stage 1 is preferably conducted by contacting the reduction gas with the catalyst for 0.5 to 600 seconds.

The reduction gas of Stage 1 is preferably provided by 10% to 200% of metal molar flow rate of the catalyst.

The reduction gas of Stage 1 preferably comprises at least one selected from hydrogen, carbon monoxide, and C1 to C4 hydrocarbon.

The reduction gas of Stage 1 preferably utilizes the byproduct generated during producing the olefin from the hydrocarbon at Stage 2.

It is effective for the olefin production method of the present invention that the pretreatment of Stage 1 is conducted at the temperature of 500° C. to 650° C.

The lower part temperature of Riser is preferably 500 to 750° C. for the olefin production method of the present invention.

The hydrocarbon mixture as the feedstock of the present invention preferably contains not less than 90 wt % of propane.

The catalyst used for the olefin production method of the present invention is an alumina type compound which can conduct the dehydrogenation reaction. Preferably, a metal component and an alkali metal are simultaneously impregnated on $Zr-Al_2O_3$ support.

The mean size of the catalyst is 20-200 micron, preferably 60-120 micron.

The residence time of hydrocarbon mixture in Riser is 0.1 to 500 seconds, preferably 0.1-50 seconds, more preferably 0.5-5 seconds.

At Stage 2 of the olefin production method of the present invention, a weight ratio of the weight of the catalyst, which is recycled to Riser bottom, divided by the weight of the hydrocarbon mixture is 10-100, preferably 20-60.

Fast Fluidization Regime of Stage 2 is the steady state that the gas flow rate is maintained over Turbulent Fluidization Regime and under Lean phase Fluidization with Pneumatic Conveying Regime, and the fixed amount of the catalyst is continuously provided to Riser, wherein dense region of lower Riser and dilute region of upper Riser exist.

In Fast Fluidization Regime, it is preferable that (a) the gas flow rate is maintained over the required value for the catalyst continuously provided into lower Riser to be entrained and exit to upper Riser smoothly, and (b) the difference of catalyst volume fractions between both points is maintained over 0.02 by controlling the gas flow rate and the catalyst circulating rate.

More preferably, the difference of the catalyst volume fractions between ¼ point and ¾ point of the lower part in Riser is between 0.047 and 0.103.

The pressure of Riser is preferably maintained at −1 to 5 $kg/cm^2 \cdot g$.

The present invention can more efficiently improve the olefin production by applying novel catalyst and the reduction pretreatment to the circulating fluidized bed process using the fast fluidized bed to improve the selectivity and the yield.

Also, by the reduction pretreatment, the present invention can prevent the hydrocarbon to contact with catalyst at an early reaction stage from being converted to useless byproduct, can help the conversion process from the hydrocarbon to the olefin, can efficiently utilize the catalyst, and can decrease the equipment investment cost by diminishing useless equipment load. And, because the catalyst is directly heated by the catalytic reaction of the pretreatment process, the energy cost to increase the catalytic reaction temperature is more reduced than the traditional indirect heating method.

DETAILED DESCRIPTION

As mentioned above, the method of the present invention comprises: (Stage 1) pretreating the catalyst by providing the reduction gas to the alumina type catalyst to produce the olefin from the hydrocarbon including more than 90 wt % of LPG; (Stage 2) producing the olefin by providing the catalyst pretreated at Stage 1 into Riser of Fast Fluidization Regime to dehydrogenate the hydrocarbon; (Stage 3) separating the mixture of produced propylene and the catalyst used at Stage 2, and regenerating the catalyst; and (Stage 4) recycling the catalyst regenerated at Stage 3 to the process of Stage 1.

Hereinafter, the present invention will be described in more detail by referring to the attached figures. However, the examples of the present invention can be modified to other different type. It is to be understood, that these examples are not to be construed to limit the scope of the present invention.

In order to explain the present examples, the same name and the same numeral are used for the same constitution, and thus overlapped additional explanation will be skipped in the following. The scale ratio will not be applied to the figures referred in the following.

Figure 1:
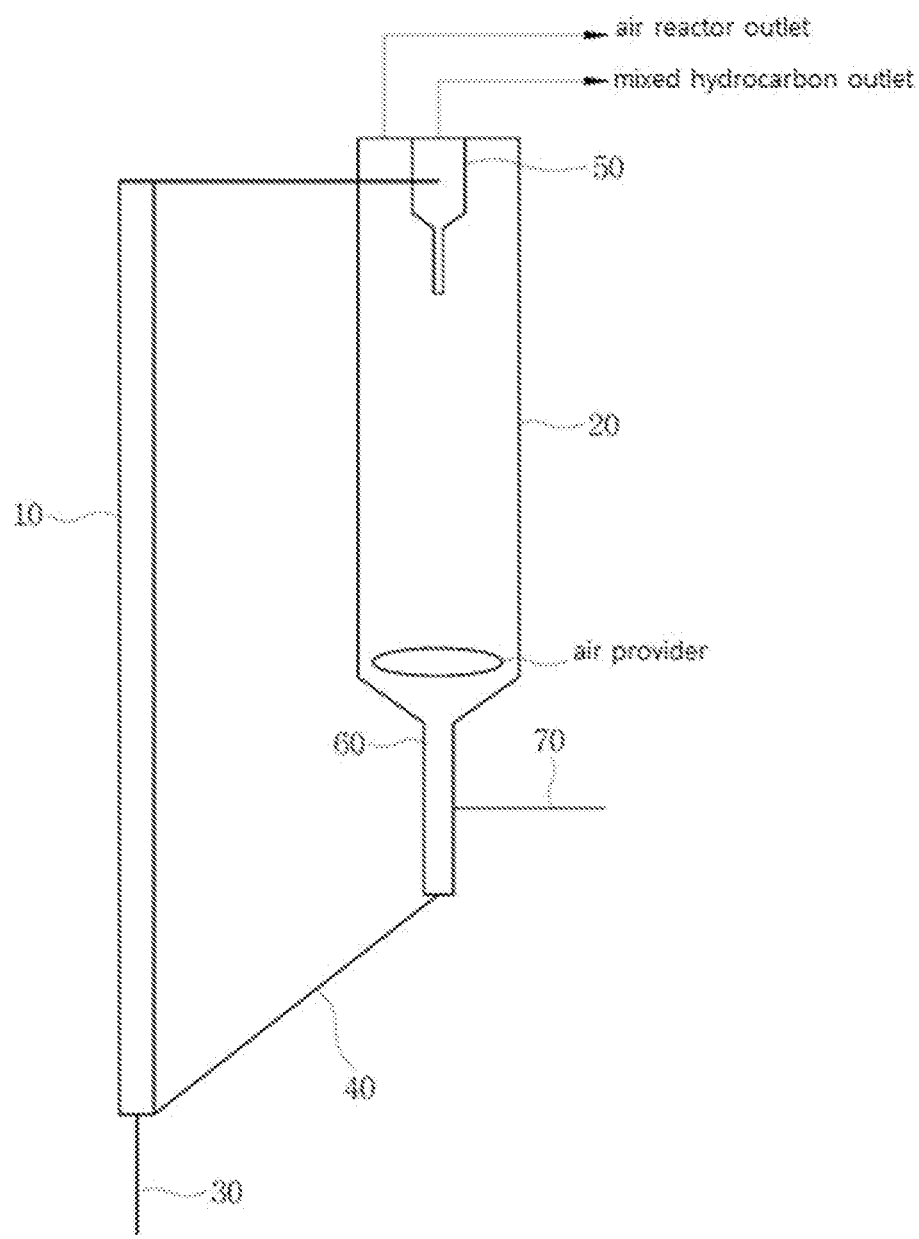
FIG. 1 is a schematic diagram of the equipment to conduct the production method of the present invention.
Figure 2:
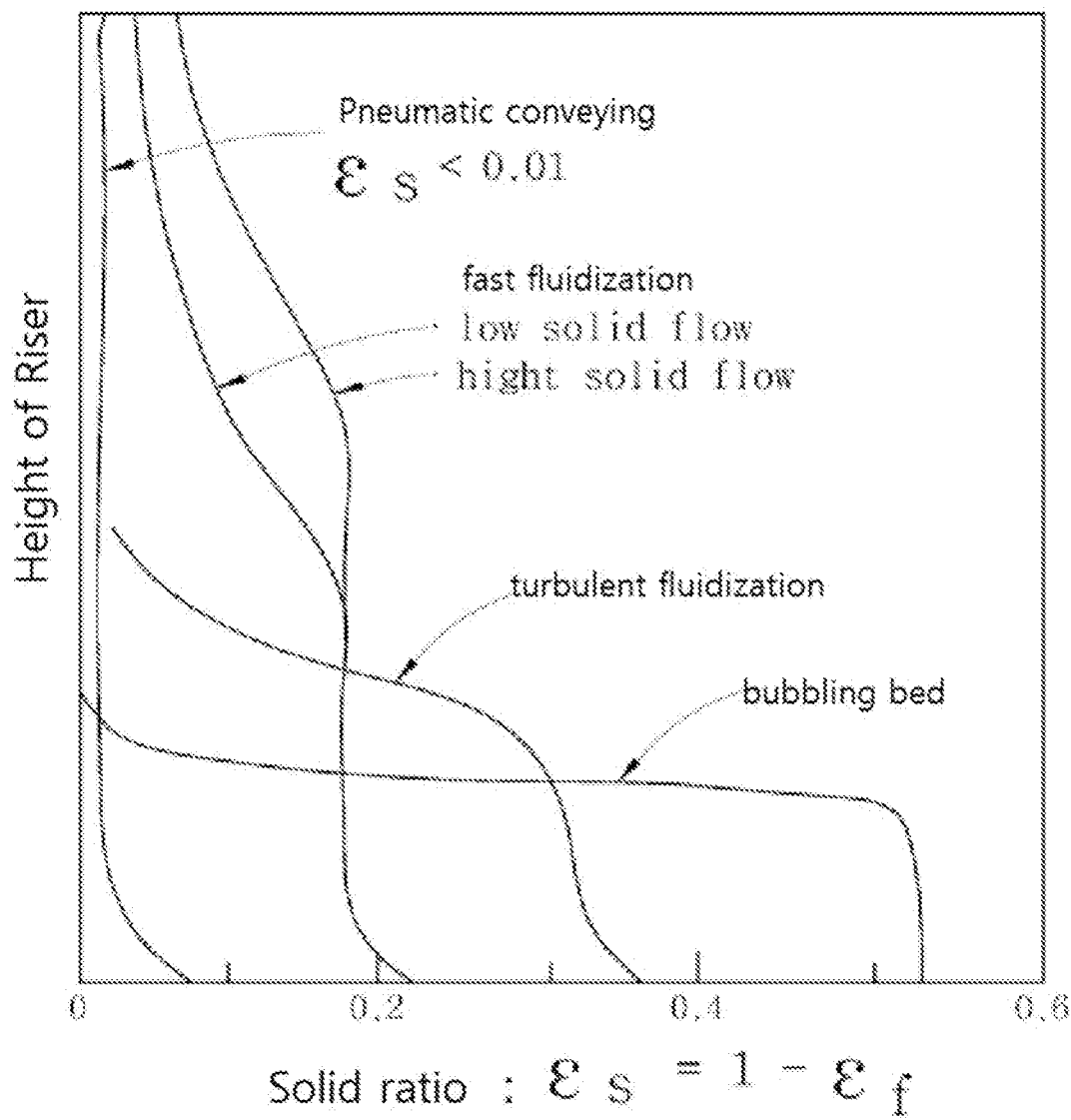
FIG. 2 is a graph describing correlation between the catalyst volume fraction and the height of Riser.
Figure 3:
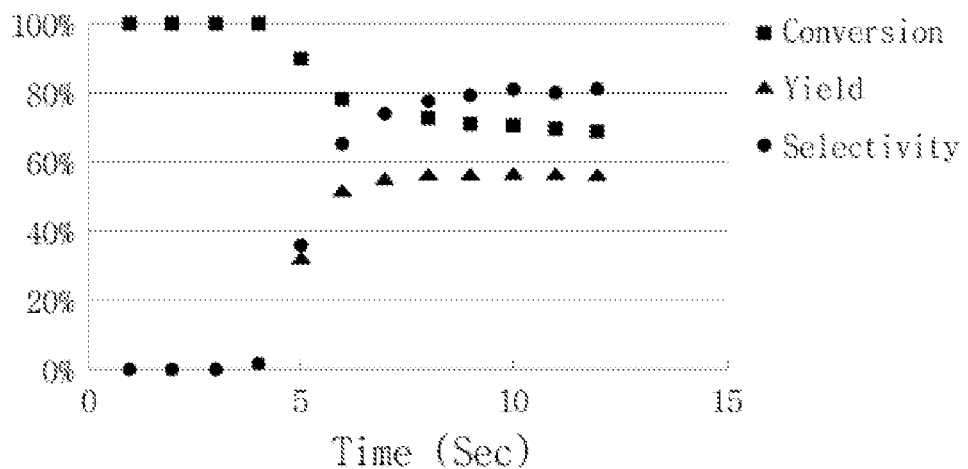
FIG. 3 is a graph describing the conversion rate, the selectivity and the yield of Comparative example 1.
Figure 4:
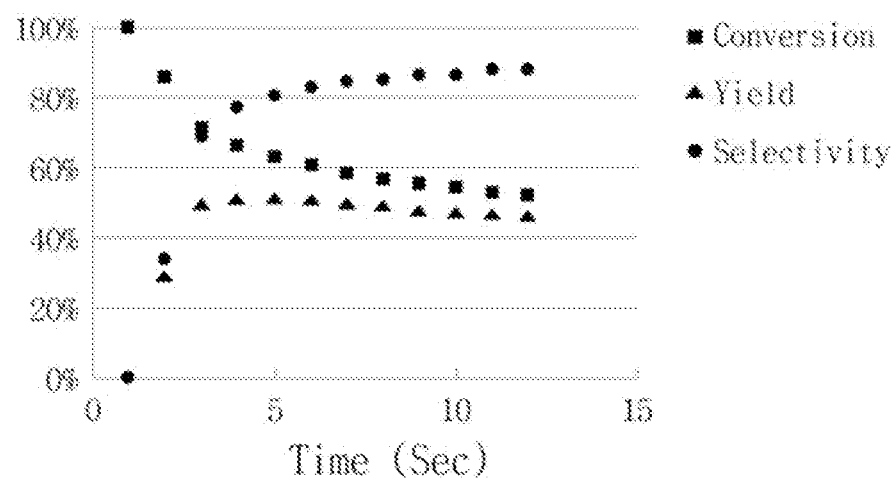
FIG. 4 is a graph describing the conversion rate, the selectivity and the yield of Comparative example 2.
Figure 5:
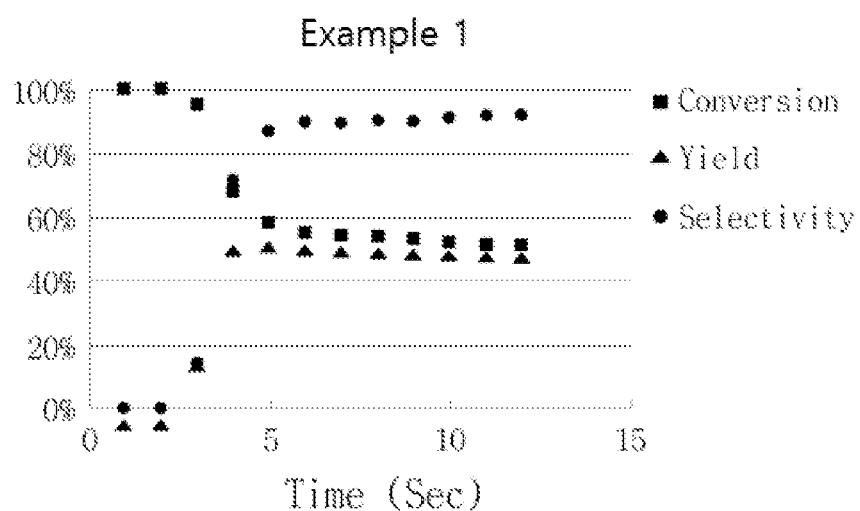
FIG. 5 is a graph describing the conversion rate, the selectivity and the yield of Example 1.
Figure 6:
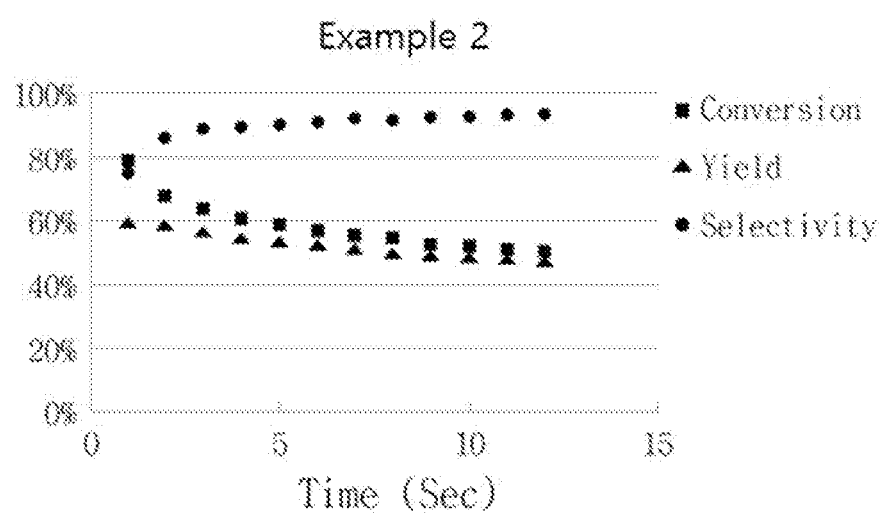
FIG. 6 is a graph describing the conversion rate, the selectivity and the yield of Example 2.
Figure 7:
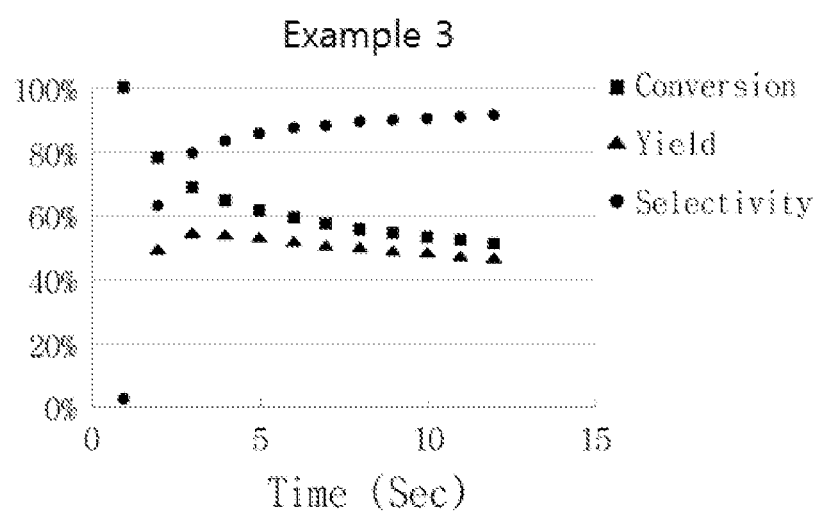
FIG. 7 is a graph describing the conversion rate, the selectivity and the yield of Example 3.

Stage 1 of the present invention is related to pretreating the catalyst by providing the reduction gas to the catalyst for producing the olefin from the hydrocarbon. As shown in FIG. 1, the reduction gas which can exothermically react with the activated oxygen species of the catalyst is provided to Catalyst Pretreater (60) through Reduction Gas Provider (70).

The method of the present invention is especially related to the dehydrogenation method to produce the olefin from the hydrocarbon. Particularly, the method of the present invention can be used to propylene production process to dehydrogenate propane. When producing the olefin, typically a catalyst, specifically a metal oxide catalyst is used. When traditionally producing the olefin from the hydrocarbon by a catalyst, the catalyst temperature tends to be rapidly increased at an early reaction stage as reaction time goes, after this, the temperature is gradually decreased.

When investigating the catalyst temperature change according to the time, the conversion rate and the olefin selectivity, the conversion rate reaches 100% at an early reaction stage that the catalyst temperature increases, but carbon dioxide is mainly generated with the oxidation reaction of the hydrocarbon feedstock. That is, the byproduct other than the olefin is produced from the hydrocarbon at an early reaction stage that the catalyst temperature increases, but the olefin is produced from the hydrocarbon from the time that the catalyst temperature gradually decreases.

Therefore, it is understood that when producing the olefin from the hydrocarbon, an early stage of the reaction during 5 seconds from the reaction initiation point is the useless part for producing the olefin.

Thus, in order to prevent the decrease of the catalyst efficiency caused by the reaction region to generate carbon dioxide as the byproduct in the traditional technology, the method of the present invention pretreats the catalyst at Stage 1 by providing the reduction gas to the catalyst for producing the olefin from the hydrocarbon.

The pretreatment of Stage 1 is created from the discovery that the byproduct is generated from the starting point that the catalyst temperature rises. If the catalyst is pretreated in advance before providing it to the hydrocarbon and thus the catalyst temperature rising region precedes, the olefin can be promptly produced without the byproduct generation region during providing the catalyst to the hydrocarbon.

The Pretreatment of Stage 1 is preferably conducted by contacting the hydrocarbon with the catalyst for 0.5 to 600 seconds. The time range of conducting the contact is roughly specified by the time range required for the increase of the catalyst temperature. By this, the catalyst can be pretreated to be an optimal state for producing the olefin.

However, under 0.5 second of the contact time of the catalyst with the reduction gas, the optimization of the catalyst cannot be accomplished. And, the olefin yield decreases when the contact time of the catalyst with the reduction gas is over 600 seconds.

The amount of the reduction gas of Stage 1 is provided within 10% to 200% of the mole of metal peroxide generated from the regeneration process of the catalyst. When using the process byproduct gas for the reduction gas, in detail, the range of 20% to 150% is more preferable. When the amount of the reduction gas is less than 10% of the mole of metal peroxide of the catalyst, the catalyst peroxide can remain. And thus the selectivity is reduced by the oxidative dehydrogenation as the side reaction during the dehydrogenation reaction. When the amount of the reduction gas is more than 200% of the mole of metal peroxide of the catalyst, the loss of fuel gas that is usable as the reduction gas occurs and the total economic efficiency is decreased.

The reductant amount of the above range can be changed according to the reduction temperature and the reductant composition, and according to the amount of the remained oxygen molecule at air regeneration process. Therefore, it is preferable that appropriate reductant amount is determined by temperature-programmed reduction (TPR) of the catalyst metal peroxide and the measurement of residual oxygen molecule after the regeneration process.

The reduction gas amount can be varied according to a kind of gas. The reduction gas preferably comprises at least one selected from hydrogen, carbon monoxide and C1 to C4 hydrocarbon. The reduction gas can react with oxygen on the catalyst surface having high reactivity and thus pretreat the catalyst. The catalyst temperature is raised by the exothermic heat of the pretreatment.

For example, the catalyst of Stage 1, for example, the metal oxide catalyst reacts with hydrogen as a kind of the reduction gas to conduct the chemical reaction of $M_xO_y + H_2 \rightarrow M_xO_y + H_2O$. The above reaction is the exothermic reaction to generate water, which can raise the catalyst temperature. The oxidative number of the catalyst is reduced at this pretreatment process.

As the reduction gas of Stage 1, it is preferable to use the byproduct generated during producing the olefin from the hydrocarbon at Stage 2. When producing the olefin from the hydrocarbon, typically carbon monoxide, hydrogen, ethylene, ethane, methane, etc., is generated as the byproduct. In the method of the present invention, hydrogen, methane, etc., generated as the byproduct, can be used for the reduction gas to pretreat the catalyst. By this, there is an effect that the production process cost is reduced.

In the olefin production method of the present invention, the pretreatment of Stage 1 is preferably conducted at the temperature range of 500° C. -650° C. When the reduction gas is provided at less than 500° C., the reduction is not sufficient. When the reduction is conducted at not less than 650° C., it can cause the side reaction of the thermal decomposition because the temperature of the reaction starting point of feedstock in lower Riser is excessively high.

The pretreatment stage of Stage 1 can be divided into two stages based on the difference of the reduction gas injection point as follows:

(a) Reduction treatment from the end of regeneration from Stand Pipe to Catalyst Provider, and
(b) Reduction treatment from Catalyst Provider to the bottom of Riser.

The reduction gas of (a) is introduced as the transfer gas having the direction from Catalyst Provider to catalyst Regenerator (20) to induce carbon dioxide generated after contacting with the catalyst or the trace unreacted reduction gas to the Regenerator to be accordingly discharged. The reduction gas of (b) is introduced as the transfer gas having the direction from Catalyst Provider (40) to Riser. In case of the reduction gas of (b), it is preferable to use the reaction feedstock as the reduction gas because generated carbon dioxide or the trace unreacted reduction gas can be mixed into the catalytic reactor to cause the side reaction.

In the method of the present invention, Stage 2 is related to the stage to produce the olefin from the hydrocarbon by using the catalyst pretreated at Stage 1. As shown in FIG. 1, the catalyst pretreated with the reduction gas in Catalyst Pretreater (60) is provided through Catalyst Provider (40) to Riser (10). In Riser (10), the olefin production reaction is conducted by dehydrogenating the hydrocarbon provided from Hydrocarbon Provider (30).

Because the catalyst of Stage 2 of the present invention is pretreated with the reduction gas before reacting with the hydrocarbon, it can produce the olefin more effectively compared to the conventional catalyst which is inputted to the olefin production process without the pretreatment. Furthermore, according to the present invention, the selectivity of the olefin production stage is increased. The selectivity is not less than 78%, more preferably not less than 89%.

That is, as mentioned above, there is a demerit that the useless byproduct is generated for a short time to increase the catalyst temperature in the olefin production. However, because of the pretreatment of Stage 1, the heated catalyst can produce the olefin from the hydrocarbon without the range to generate the byproduct. In result, the olefin can be produced massively, and the efficiency is more enhanced in respect of the process economic effects.

The hydrocarbon feedstock is provided through Hydrocarbon Provider (30), and it can be pre-heated to 500-600° C. for more efficient reaction. The feedstock is mixed with the reduction treatment gas from Catalyst Provider to the bottom of Riser, and is introduced into the reaction region of Riser (10), and is mixed with the catalyst provided through Catalyst Provider (40) in the bottom of Riser (10).

Meanwhile, the catalyst used at the process is regenerated in Regenerator (20). The regenerated catalyst is pretreated with the reduction gas in Catalyst Pretreater (60) and is provided through Catalyst Provider (40) to Riser (10). At this time, the lower part temperature of Riser is preferably maintained at 500-750° C. When the lower part temperature of Riser is less than 500° C., the catalyst conversion rate becomes to be decreased. Moreover, when the temperature is more than 750° C., the catalyst selectivity becomes to be decreased due to the increment of the byproduct generated from the thermal decomposition of LPG feedstock.

The feedstock is completely gasified by the heat from the pretreated catalyst in addition to the heat provided by regenerated catalyst in this way, and is raised to the temperature needed for the dehydrogenation reaction.

Subsequently, the feedstock and the catalyst mixed in the lower part of Riser (10) cause the dehydrogenation reaction and are fluidized to flow upwards. At this time, the mixture temperature is decreased as the endothermic reaction of the dehydrogenation proceeds, and the upper part temperature of Riser (10) is relatively further decreased. The reaction product and the catalyst reached to the upper part of Riser (10) are introduced to Separator (50), therefore the gaseous reaction product and the solid catalyst are separated in a short time. In order to enhance the separation efficiency, a cyclone can be selectively used. The separated gaseous reaction product is discharged through Mixed hydrocarbon outlet, and the separated catalyst is stacked in Separator (50) and moved to downwards. At this time, air is provided into the lower part of Separator (50) and eliminates the unseparated hydrocarbon product during moving upwards in Separator (50). These are discharged to Mixed hydrocarbon outlet.

The catalyst in the lower part of Separator (50) is moved to Regenerator (20). At this time, the catalyst can comprise the coke generated in the reaction. The gas flow such as air is introduced into the lower part of Regenerator (20), the coke included in the catalyst reacts with oxygen at the high temperature over 600° C. to be converted into carbon monoxide or carbon dioxide, and consequently the coke amount included in the catalyst is reduced prominently.

In the process of the present invention, the hydrocarbon compound, specifically the hydrocarbon mixture comprising not less than 90% of LPG can be used as the feedstock. The hydrocarbon mixture preferably comprises over 90 wt % of propane.

The catalyst used for dehydrogenating the feedstock in the present invention can generally convert the hydrocarbon compound into the olefin through the dehydrogenation reaction. The catalyst is not limited to the specific one if it is well known in the pertinent art. It is the alumina type compound capable of the dehydrogenation, preferably $Zr—Al_2O_3$ support impregnated with the metal component and the alkali metal at the same time.

The mean size of the catalyst is 20-200 micron, preferably 60-120 micron. In order to achieve the high efficient catalyst reaction, proper flow of Fast Fluidization Regime within Turbulent Fluidization Regime and Lean phase Fluidization with Pneumatic Conveying Regime is required. However, when using the catalyst of smaller than 20 micron, the yield can be decreased due to the high space velocity because Lean phase Fluidization with Pneumatic Conveying Regime is predominant. Besides, when using the catalyst of larger than 200 micron, the yield can be decreased because Turbulent Fluidization Regime is formed. Also, because of very slow circulating fluidization flow, the production rate of the product is decreased. In order to maintain the same productivity, very huge catalytic reaction equipment is required and thus the investment cost is increased.

Furthermore, in case of the dehydrogenation process to produce the olefin by using the above catalyst, the residence time of the reactant in Riser can be an important reaction condition to determine the olefin yield and the composition. Because the number of the gas molecules and the flow rate varies as the dehydrogenation proceeds in Riser, a criteria to determine the residence time is needed. Therefore, for the residence time of the reactant in the present invention, the value of Riser volume divided by volume velocity of gas discharged from the upper part of Riser is used as the criteria.

In the dehydrogenation process of the present invention, the effective residence time of the hydrocarbon raw compound in Riser is 0.01-500 seconds, preferably 0.1-50 seconds, more preferably 0.5-5 seconds. When the residence time is less than 0.1 second, the sufficient contact time of the catalyst and the hydrocarbon feedstock is not secured so that the product yield is decreased. When being more than 500 seconds, the excessive investment cost for reactor equipment is required to develop Fast Fluidization Regime needed in the present invention.

The fluidized dehydrogenation in the present invention is the endothermic reaction. The catalyst recycle of high temperature becomes to provide the heat needed for the reaction. Therefore, at Stage 2 more appropriate to this purpose of the present invention, the weight ratio of the catalyst weight divided by the weight of hydrocarbon mixture, which are provided into the lower part of Riser, is 10-100, preferably 20-60.

When the weight ratio is less than 10, because the space velocity of the catalyst relative to the hydrocarbon feedstock becomes too high, the sufficient contact time for the reaction cannot be secured. When the weight ratio is more than 100, the excessive investment cost for reactor equipment is required to embody Fast Fluidization Regime needed in the present invention. Furthermore, the excessive flow rate is induced in Catalyst Regenerator so that the sufficient regeneration time is not secured. Therefore, the weight ratio within the above range of the proper catalyst weight divided by the weight of the hydrocarbon mixture is required.

According to the circulating fluidized bed process of the present invention, in order to effectively produce the olefinic hydrocarbon compound from the hydrocarbon raw mixture, it is important to provide the sufficient volume fraction and the distribution of the catalyst capable of the dehydrogenation by maintaining the fluidization region of Riser to be Fast Fluidization Regime.

Fast Fluidization Regime of Stage 2 in the present invention is the steady state that the gas flow rate in Riser is maintained over Turbulent Fluidization Regime and under Lean phase Fluidization with Pneumatic Conveying Regime, and the fixed amount of the catalyst is continuously provided to Riser, wherein dense region of lower Riser and dilute region of upper Riser exist.

And, in Fast Fluidization Regime, it is preferable that (a) the gas flow rate is maintained over the required value for the catalyst continuously provided into lower Riser to be entrained and exit to upper Riser smoothly, and (b) the difference of catalyst volume fractions between both points is maintained not less than 0.02 by controlling gas flow rate and catalyst circulating rate.

More preferably, the difference of the catalyst volume fractions between ¼ point and ¾ point of the lower part in Riser is between 0.047 and 0.103. The catalyst of the present invention shows high efficient catalytic reactivity especially at Fast Fluidization Regime. When the volume fraction difference is less than 0.047, because it approaches Lean phase Fluidization with Pneumatic Conveying Regime, the yield reduction can be incurred by the high space velocity.

When the difference of the volume fraction is more than 0.103, because of very slow circulating fluidization flow, the production speed of the product is decreased. In order to maintain the same productivity, very huge catalytic reaction equipment is required so that the investment cost is increased.

It is preferable that Riser is maintained at the pressure of −1 to 5 kg/cm$^2$·g. The pressure of Riser represents the reaction pressure. When it is less than −1 kg/cm$^2$·g, the compression energy for separating the product from produced material is increased and the investment cost for compression equipment is also increased so that the total economic efficiency decreases. Also, when it is more than 5 kg/cm$^2$·g, although the investment cost for compression equipment and the compression energy is reduced at the latter part of the reactor, the product yield is decreased because of the inducement of the high pressure reaction. Therefore, the appropriate pressure of Riser within the above range is needed.

The olefin produced in Riser is separated from the used catalyst in Separator (50) and is obtained. The catalyst separated in Separator (50) is provided to Regenerator (20) and is regenerated. Also, the catalyst regenerated in Regenerator (20) is recycled again to Catalyst Pretreater (60), and is provided again to Riser (10) after the pretreatment.

Hereinafter, the present invention will be explained in more detail referring to specific examples.

The catalyst used for the examples is [(5% Cr+0.5% K)/5% Cr/Zr—Al$_2$O$_3$]. Volume mean diameter of the catalyst is 84 micron. Particle size distribution is composed of 10% of not more than 60 micron, 90% of 60-100 micron, and 10% of not less than 100 micron.

A. CATALYST PREPARATION (1) Support (Zr—Al$_2$O$_3$) Preparation

Catapal B (alumina sold by Sasol) 13.89 kg added with water 25 kg is agitated for 30 minutes, and 1.83 kg of ZrO(NO$_3$)$_2$ and 25 kg of water is mixed and further agitated for 2.5 hours. Then, it is spray dried (feed velocity 0.56 g/min, atomizer 6000 rpm, inlet temperature 208° C., outlet temperature 125° C.), sieving separated (sieving: 75-200 μm), and calcined at 650° C. for 6 hours.

(2) Catalyst [(5% Cr+0.5% K)/5% Cr/Zr—Al$_2$O$_3$] preparation 0.482 g of CrO$_3$ and 2.5 g of water is mixed and impregnated with 5 g of the support as prepared above, dried at 120° C., and calcined at 700° C. for 3 hours (pre-catalyst).

0.482 g of CrO$_3$, 0.068 g of KNOB and 2.5 g of water is mixed and impregnated with 5.25 g of 5% Cr/Zr—Al$_2$O$_3$ as prepared above, dried at 120° C., and calcined at 700° C. for 3 hours so that the catalyst of the present invention is prepared.

B. CONSTITUTION OF THE CIRCULATING FLUIDIZED BED

As shown in FIG. 1, in order to measure the activity of the catalyst during the olefin production, the circulating fluidized bed process is used. The circulating fluidized bed process is consisted of Riser, Regenerator and Separator. The height of Riser is 6.5 m, and its diameter is 0.94 cm. The height of Regenerator is 1.5 m, and its diameter 12 cm. The height of Separator is 2 m, and its diameter is 10 cm.

At Riser inlet, the feedstock of the hydrocarbon mixture comprising not less than 90% of LPG, dilution gas and the catalyst are introduced and mixed. The reaction temperature is maintained at 640° C. The space velocity (WHSV: ml/gcat.hr) is maintained at 8400 or 4240. Catalyst injection amount is 88.1 kg/m2.s by considering cross-sectional area of Riser.

C. EXAMPLES

Example 1

Olefin Production 1

Stage 1: Before providing the catalyst as prepared above through Catalyst Provider to the reaction part, the pretreatment is conducted for 60 seconds by providing hydrogen (H$_2$) through Reduction Gas Provider to Catalyst Pretreater. The temperature of the catalyst passing by Catalyst Provider is increased by 10° C. to 40° C. due to the pretreatment to reach to about 640-660° C.

Stage 2: The catalyst heated at Stage 1 is provided to Riser to become 4240 of space velocity (WHSV: ml/gcat.hr), and propane is provided through Hydrocarbon Provider to Riser so that propylene is produced.

Stage 3: Propylene produced at Stage 2 and the reacted catalyst is separated in Separator to obtain propylene, and the reacted catalyst is recycled to Regenerator to be regenerated.

Stage 4: The catalyst regenerated in Regenerator undergoes repeatedly the process of Stage 1, and is provided to Riser.

Example 2

Olefin Production 2

Except for changing the reduction time to 300 seconds at Stage 1 of Example 1 of the present invention and changing the space velocity (WHSV: ml/gcat.hr) to 8400, the same process of Example 1 is conducted to produce propylene.

When providing hydrogen as the reduction gas, the catalyst temperature is measured during propane dehydrogenation. As hydrogen amount is increased to pretreat oxygen species carrier, the temperature increment range of the catalyst layer caused by the rapid combustion reaction at an early stage of the dehydrogenation is decreased.

Example 3

Olefin Production 3

Except for providing methane (CH$_4$) instead of hydrogen as the reduction gas and treating for 1 second at Stage 1 of Example 1 of the present invention, the same process of Example 1 is conducted to produce propylene.

When providing methane as the reduction gas, the catalyst temperature is measured during propane dehydrogenation. As methane amount is increased to pretreat oxygen species carrier, the temperature increment range of the catalyst layer caused by the rapid combustion reaction at an early stage of the dehydrogenation is decreased.

Comparative Example 1

Except for not using the reduction gas at Stage 1 of Example 1 of the present invention, the same process of Example 1 is conducted to produce propylene.

Comparative Example 2

Except for not using the reduction gas at Stage 1 of Example 3 of the present invention, the same process of Example 3 is conducted to produce propylene.

The experimental result (FIG. 3 to FIG. 7) is compared in the following Table 1.

TABLE 1

|  | Comparative example 1 | Comparative example 2 | Example 1 | Example 2 | Example 3 |
|---|---|---|---|---|---|
| WHSV (space velocity, ml/gcat · hr) | 4240 | 8400 | 4240 | 8400 | 8400 |
| Reaction temperature (° C.) | 640 | 640 | 640 | 665 | 640 |
| Reduction gas | — | — | $H_2$ | $H_2$ | $CH_4$ |
| Reduction time (second) | — | — | 60 | 300 | 60 |
| Conversion rate (%) | 76.9 | 61.7 | 63.6 | 57.6 | 60.9 |
| Selectivity (%) | 60.4 | 73.8 | 78.7 | 89.5 | 78 |
| Propylene yield (%) | 46.5 | 45.5 | 50 | 51.6 | 47.5 |
| CO yield (%) | 7.6 | 3.9 | 4.2 | 1.5 | 3.1 |
| $CO_2$ yield (%) | 31.4 | 12.5 | 5.8 | 0 | 10.1 |

From the above experimental result, when producing propylene by using the circulating fluidized bed comprising the reduction treatment of the present invention, the selectivity increases remarkably, the byproduct yield such as carbon monoxide, carbon dioxide and water is decreased noticeably. If the present invention is applied to the real commercial process, its economic effect will be very remarkable.

In the above, although the examples of the present invention is explained in detail, the claimed scope of the present invention is not limited to the examples. It is well known to a person of ordinary skill in the pertinent art that various modifications and changes can be made within the range not deviating from the technical thought written in the claims of the present invention.

The invention claimed is:

1. An olefin production method comprising:
    pretreating a catalyst by providing a reduction gas to the catalyst, wherein the catalyst comprises alumina (Stage 1);
    producing an olefin by providing the catalyst pretreated in Stage 1 and a hydrocarbon including no less than 90 wt% of LPG into a Riser of Fast Fluidization Regime and dehydrogenating the hydrocarbon to produce an olefin comprising propylene (Stage 2);
    separating a mixture of the produced propylene and the catalyst from Stage 2, and regenerating the separated catalyst (Stage 3); and
    recycling the catalyst regenerated in Stage 3 to Stage 1 (Stage 4);
    wherein the pretreating of Stage 1 comprises introducing a first reduction gas comprising hydrogen and/or methane flowing from an end of a Catalyst Provider to an end of a Regenerator, and wherein the Catalyst Provider is fluidly connected between a bottom of the Riser and the end of the Regenerator.

2. The method of claim 1, wherein the pretreating of Stage 1 further comprises introducing a second reduction gas flowing from the Catalyst Provider to a bottom of the Riser.

3. The method of claim 1, wherein the pretreating of Stage 1 is conducted by contacting the reduction gas with the catalyst for 0.5 to 600 seconds.

4. The method of claim 1, wherein a flow rate of the reduction gas of Stage 1 is 10% to 200% of a molar flow rate of metal peroxide of the catalyst.

5. The method of claim 1, wherein the reduction gas of Stage 1 is a byproduct generated during producing the olefin from the hydrocarbon in Stage 2.

6. The method of claim 1, wherein the pretreating of Stage 1 is conducted at 500° C. to 650° C.

7. The method of claim 1, wherein a temperature of a lower part of the Riser is 500° C. to 750° C.

8. The method of claim 1, wherein the hydrocarbon contains not less than 90 wt% of propane.

9. The method of claim 1, wherein the alumina type is $Zr-Al_2O_3$ support impregnated with a metal component and an alkali metal simultaneously.

10. The method of claim 1, wherein a mean size of the catalyst is 20 to 200 micron.

11. The method of claim 1, wherein a residence time of the hydrocarbon for the dehydrogenating in the Riser is 0.1 to 500 seconds.

12. The method of claim 1, wherein in Stage 2, a weight ratio of the pretreated catalyst the hydrocarbon is 10 to 100.

13. The method of claim 1, wherein the Fast Fluidization Regime of Stage 2 is a steady state that a gas flow rate is maintained over Turbulent Fluidization Regime and under Lean phase Fluidization with Pneumatic Conveying Regime, and a fixed amount of the pretreated catalyst is continuously provided to the Riser, wherein a dense region in a lower part of the Riser and a dilute region in an upper part of the Riser exist.

14. The method of claim 13, wherein in the Fast Fluidization Regime, (a) the gas flow rate is maintained over a required value for the pretreated catalyst continuously provided into the lower part of the Riser to be entrained and exit to the upper part of the Riser smoothly, and (b) a difference of catalyst volume fractions between the lower part and the upper part of the Riser is maintained not less than 0.02 by controlling gas flow rate and catalyst circulating rate.

15. The method of claim 1, wherein a pressure of the Riser is −1 to 5 $kg/cm^2 \cdot g$.

* * * * *